(12) United States Patent
Nair et al.

(10) Patent No.: US 7,524,651 B2
(45) Date of Patent: Apr. 28, 2009

(54) ASSAY METHODS FOR DETECTION OF A VIRUS IN AN AVIAN TISSUE SAMPLE

(75) Inventors: Venugopal K. Nair, Compton (GB); Susan Jean Baigent, Compton (GB); Richard John William Currie, Ayrshire (GB)

(73) Assignee: Wyeth, Madison, NJ (US)

( * ) Notice: Subject to any disclaimer, the term of this patent is extended or adjusted under 35 U.S.C. 154(b) by 428 days.

(21) Appl. No.: 10/530,073

(22) PCT Filed: Oct. 14, 2003

(86) PCT No.: PCT/EP03/11360

§ 371 (c)(1),
(2), (4) Date: Sep. 8, 2005

(87) PCT Pub. No.: WO2004/035821

PCT Pub. Date: Apr. 29, 2004

(65) Prior Publication Data

US 2006/0269910 A1    Nov. 30, 2006

(30) Foreign Application Priority Data

Oct. 15, 2002 (GB) .............................. 0223960.6
May 29, 2003 (GB) .............................. 0312241.3

(51) Int. Cl.
*C12P 19/34* (2006.01)
*C12Q 1/70* (2006.01)
*C12Q 1/68* (2006.01)
*A61K 39/00* (2006.01)

(52) U.S. Cl. .............................. 435/91.2; 435/5; 435/6; 435/91.32; 435/91.33; 424/229.1

(58) Field of Classification Search ........................ None
See application file for complete search history.

(56) References Cited

U.S. PATENT DOCUMENTS 6,221,362 B1    4/2001    Audonnet et al.

FOREIGN PATENT DOCUMENTS

EP    0346 998 B1    6/1989
EP    0 884 382 A2   6/1998

OTHER PUBLICATIONS

Davidson et al. The feather tips of commercial chickens are a favorable sourse of DNA for the amplification of MDV and ALV-J. Avian Pathology, Jun. 1, 2002, vol. 31, No. 3, pp. 237-240.*
Handberg et al. The use of serotype 1 and serotype 3-specific PCR for the detection of MDV in chickens. Avian Pathology, Jun. 1, 2001, vol. 30, No. 3, pp. 243-249.*
Becker et al. PCR detection of amplified 132 bp repeats in MDV-1 DNA can serve as an indicator for critical genomic rearrangement leading to the attenuation of virus virulence. Virus Genes, 1993, vol. 7, No. 3, pp. 277-287.*
Burgess et al. A quantitive duplex PCR technique for measuring amounts of cell-associated MDV . . . Journal of Virological Methods, Sep. 1999, vol. 82, No. 1, pp. 27-37.*
Carrozza et al. Avian Diseases, Oct.-Dec. 1973, vol. 17, No. 4, pp. 767-781.*
Calnek et al. Avian Diseases, May 1970, vol. 14, No. 2, pp. 219-233.*
Novak, R., et al, "In situ hybridization for detection of chicken anaemia virus in peripheral blood smears", Department of Avian Medicine, College of Veterinary Medicine, University of Georgia, Athens, Georgia, Molecular and Cellular Probes (1997) 11, 135-141.
Davidson, Irit , et al, "The feather tips of commercial chickens are a favorable source of DNA for the amplification of Marek's disease virus and avian leukosis virus, subgroup J.", Avian Pathology (2002) 31, 237-240.
Rangga-Tabbu C., Cho B.R., "Marek's disease virus (MDV) antigens in the feather follicle epithelium: difference between oncogenic and nononcogenic MDV," Avian Disease, Oct.-Dec.; 26(4):907-17. 1982.
Maotani K., Kanamori A., Ikuta K., Ueda S., Hirai K., "Amplification of a tandem direct repeat within inverted repeats of Marek's disease virus DNA during serial in vitro passage," J. Virol. May; 58(2):657-60. 1986.
Silva, R.F., "Differentiation of pathogenic and non-pathogenic serotype 1 Marek's disease viruses (MDVs) by polymerase chain reaction amplification of the tandem direct repeats within the MDV genome," Avian Disease, Jul.-Sep.;36(3):521-8. 1992.
Becker, Y., Ahser Y., Tabor E., Davidson I., Malkinson, M., Weisman Y., "Polymerase chain reaction for differentiation between pathogenic and non-pathogenic serotype 1 Marek's disease viruses (MDV) and vaccine viruses of MDV-serotypes 2 and 3," J. Virol. Methods, Dec. 1; 40(3):307-22. 1992.
Rong-Fu W., Beasley J.N., Cao W.W., Slavik, M.F., Johnson M.G., "Development of PCR method specific for Marek's disease virus," Mol Cell Probes, Apr.;7(2):127-31. 1993.
Kreader, C.A., "Relief of amplification inhibition in PCR with bovine serum albumin or T4 gene 32 protein," Appl. Environ. Microbiol., Mar.;62(3):1102-6. 1996.
Forbes BA, Hicks K.E., "Substances interfering with direct detection of Mycobacterium tubervulosis in clinical specimens by PCR: effects of bovine serum albumin," J. Clin. Microbiol., Sep.; 34(9): 2125-8. 1996.
Bumstead N., Sillibourne J., Rennie M., Ross N., Davison F., "Quantification of Marek's disease virus in chicken lymphocytes using the polymerase chain reaction with fluorescence detection," J. Virol. Methods, Apr.; 65(1):75-81. 1997.
Niikura M., Witter R.L., Jang H.K., Ono M., Mikami T., Silva R.F., "MDV glycoprotein D is expressed in the feather follicle epithelium of infected chickens," Acta. Virol. Apr.-Jun.;43(2-3)159-63. 1999.
Iddekinge van BJ, Stenzler L., Schat K.A., Boerrigter H., Koch G., "Genome analysis of Marek's disease virus strain CVI-988: effect of cell culture passage on the inverted repeat regions," Avian Dis. Apr.-Jun.;43(2):182-8. 1999.
Reddy S.M., Witter R.L., Gimeno I., "Development of a quantitative-competitive polymerase chain reaction assay for serotype 1 Marek's disease virus," Avian Disease, Oct.-Dec.;44(4):770-5. 2000.
Davidson I., Borenshtain R., Weisman Y., "Molecular identification of the Marek's disease virus vaccine strain CVI988 in vaccinated chickens," J. Vet. Med. B Infect. Dis. Vet. Public Health, Mar.; 49(2):83-7. 2002.
Borenshtain R., Davisdon, I. "Marek's disease virus genome separation from feather tip extracts by pulsed field gel electrophoresis," J. Virol. Methods, Mar.; 101(1-2):169-74, 2002.
Van der Heijden, H.M., Bakker J., Elbers A.R., Vos J.H., Weyns, A., de Smet M. Mc Orist S., "Prevalence of exposure and infection of Lawsonia intracellularis among slaughter-age pigs," Res. Vet. Sci., Dec.;77(3)197-202. 2004.

* cited by examiner

*Primary Examiner*—Bruce Campell
*Assistant Examiner*—Sharon Hurt
(74) *Attorney, Agent, or Firm*—Frank R. Cottingham

(57) ABSTRACT

The invention relates to methods of detecting a virus in an avian tissue sample wherein genetic material derived from feathers is tested for the presence of genetic material from the virus.

15 Claims, 11 Drawing Sheets

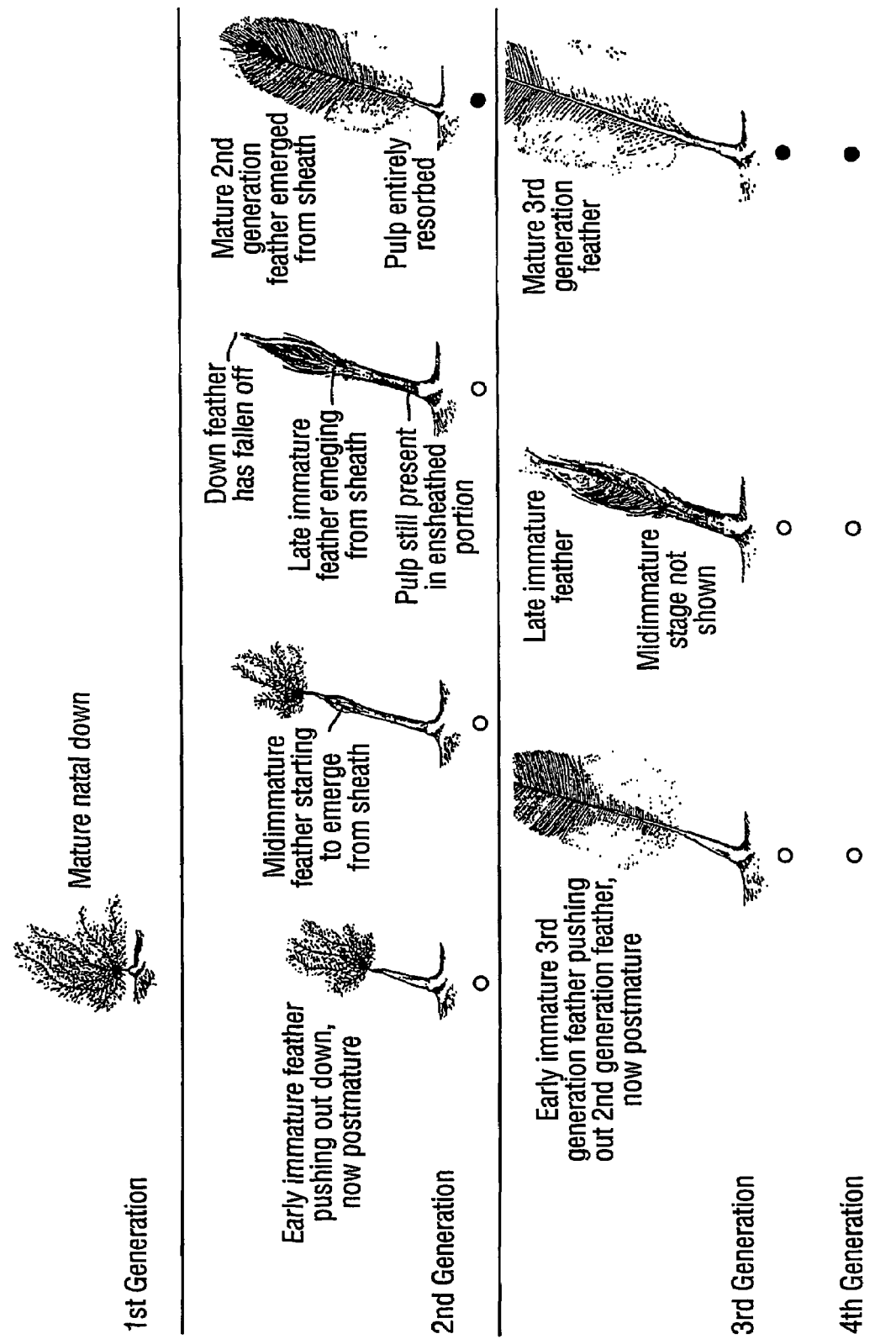

Fig.1(b)
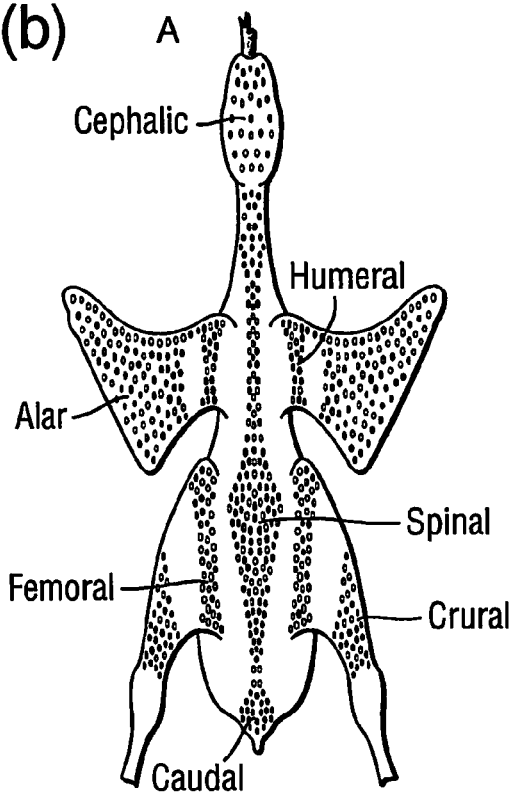
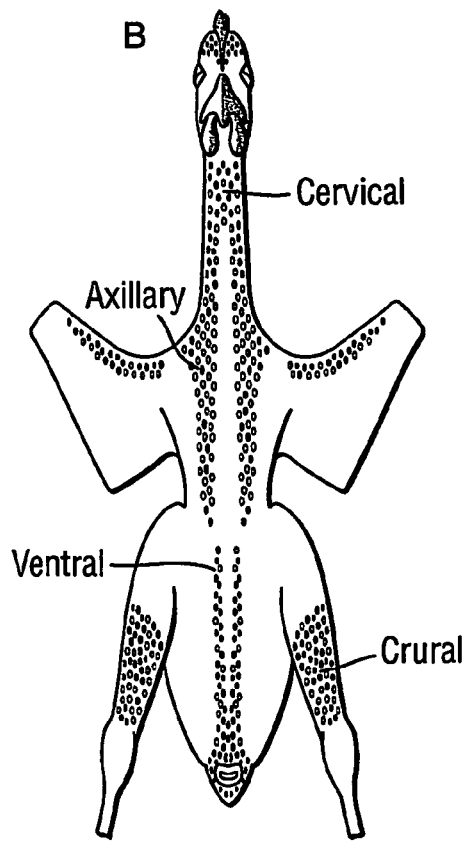

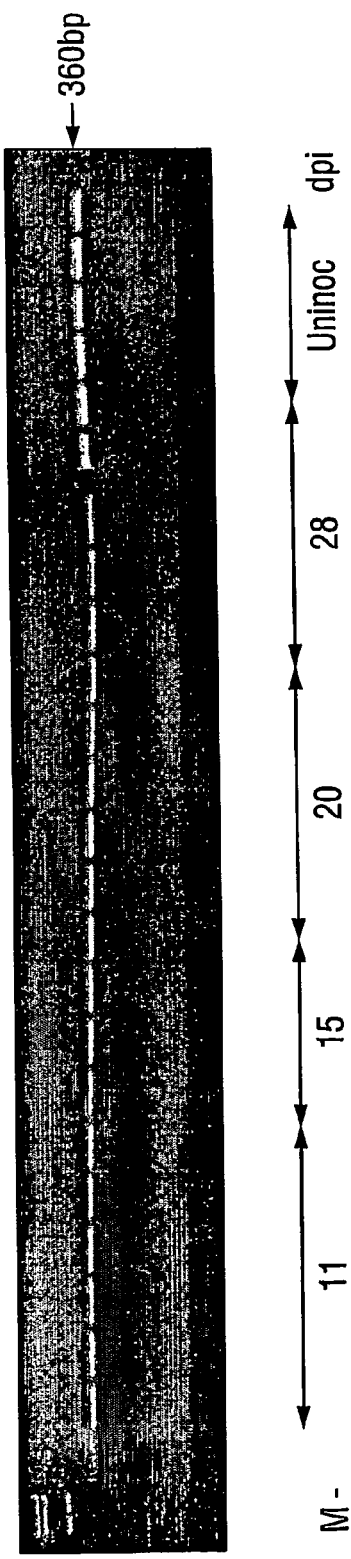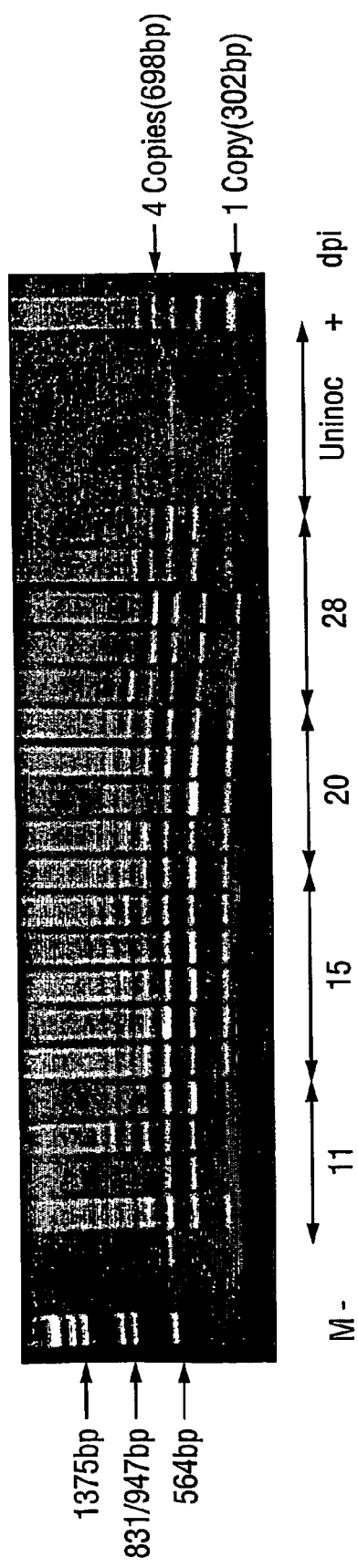

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: DNA Probe

<400> SEQUENCE: 1
agaccctgat gatccgcatt gcgact                26

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA Primer

<400> SEQUENCE: 2
ggtctggtgg tttccaggtg a                21

```
<210> SEQ ID NO 3
<211> LENGTH: 21
<212> TYPE: DNA
<213> ORGANISM: Artificial Sequence
<220> FEATURE:
<223> OTHER INFORMATION: DNA Probe

<400> SEQUENCE: 3
gcatagacga tgtgctgctg a                                              21

<210> SEQ ID NO 4
<211> LENGTH: 24
<212> TYPE: DNA
<213> ORGANISM: Artificial Sequence
<220> FEATURE:
<223> OTHER INFORMATION: DNA Probe

<400> SEQUENCE: 4
tacttcctat atagattgag acgt                                           24

<210> SEQ ID NO 5
<211> LENGTH: 24
<212> TYPE: DNA
<213> ORGANISM: Artificial Sequence
<220> FEATURE:
<223> OTHER INFORMATION: DNA Probe

<400> SEQUENCE: 5
gagatcctcg taaggtgtaa tata                                           24

<210> SEQ ID NO 6
<211> LENGTH: 19
<212> TYPE: DNA
<213> ORGANISM: Artificial Sequence
<220> FEATURE:
<223> OTHER INFORMATION: DNA Probe

<400> SEQUENCE: 6
cactgccact gggctctgt                                                 19

<210> SEQ ID NO 7
<211> LENGTH: 21
<212> TYPE: DNA
<213> ORGANISM: Artificial Sequence
<220> FEATURE:
<223> OTHER INFORMATION: DNA Probe

<400> SEQUENCE: 7
gcaatggcaa taaacctcca a                                              21

<210> SEQ ID NO 8
<211> LENGTH: 27
<212> TYPE: DNA
<213> ORGANISM: Artificial Sequence
<220> FEATURE:
<223> OTHER INFORMATION: Synthetic DNA Primer

<400> SEQUENCE: 8
agtctggaga agtctgtgca gcctcca                                        27

<210> SEQ ID NO 9
<211> LENGTH: 2466
<212> TYPE: DNA
<213> ORGANISM: Marek's Disease Serotype 1
```

<400> SEQUENCE: 9

```
gaattcggtg atataaagac gatagtcatg catgacgtgg ggggctggat cgactgatat      60
ctaatggttc gggagtgata cggagacggg ggggggggg aaatgatcga tttatacta      120
cctcttaaat aaactattgc tcctttataa aatgacaggt gaattgtgac cgttcgcgaa     180
cgtgtaattc ttcaatactt tcgggtctgt gggtgttgct ttttaatta ttattttggt      240
tcggggaggt tggtgctgga atgttaagaa taaattccgc acactgattc ctaggcaggc     300
gtctcttgca ggtgtatacc agggagaagg cgggcacggt acaggtgtaa agagatgtct     360
caggagccag agccgggcgc tatgccctac agtcccgctg acgatccgtc cccctcgat     420
ctttctctcg ggtcgacttc gagacggaaa aaaggaaaa gtcacgacat ccccaacagc      480
ccctccaaac acccctcc tgacggccta tctgaggagg agaaacagaa gctgaaagg       540
aggagaaaaa ggaatcgtga cgccgctcgg agaagacgca ggaagcagac ggactatgta     600
gacaaactcc atgaagcatg tgaagagctg cagagggcca atgaacacct acgtaaggaa     660
attcgagatc taaggactga gtgcacgtcc ctgcgtgtac agttggcttg tcatgagcca     720
gttttgcccta tggcggtacc cccttggtg accctggac tgcttaccac cccgcacgat      780
cccgttcctg aacctcccat ttgcactcct ccacctccct caccggatga acctaacgct     840
ccacattgct ccggttccca acctcctatc tgtaccccc ctcctcccga tacgaggaa       900
ctttgcgccc agctctgctc gaccccacca cctccatct ctactccca tattatctac      960
gctccgggc cttccccct ccaacctcct atctgtaccc ccctctcc cgatgcggag      1020
gagctttgcg cccagctctg ctcgacccca ccacctccca tctgtactcc ccattccctc    1080
ttctgccctc cccagcctcc atctccggag ggaatcttcc ctgcattgtg tcctgttacc    1140
gagccgtgta cccctccatc gccggggacg gtttacgctc agctttgtcc tgttggccag    1200
gctccctttt ttaccccatc tccccacat ccggctccgg agccggagag cttatgct      1260
cgtcttaccg aggatcccga acaggattcc ttgtattcgg gccagattta tattcagttt    1320
ccctcggata ctcagtctac ggtctggtgg tttccaggtg acgggagacc ctgatgatcc    1380
gcattgcgac tctcagcagc acatcgtcta tgccccatgt ttcttctccc ctagttatat    1440
ataatagttt tcatagttc gggaagatca acataaagga aagggttaaa ggcattattt     1500
atcgatttac tgacataaaa aaatcctctg gggtaacaaa ttttccctta ccgtgtagct    1560
tagactcgga agaactattt taagttacat ggtcaaaaga tttgttggct ccaggagttc    1620
cgaagtatga gataaactta gctatgtgga aaacttctgg ggcaacatct ctcggcccca    1680
gactgcttaa atggcaaatt tcgttctat acagaacggt tggggaaggg ggggggggg     1740
gtatatggag tattattcgg gatatggctt ctatgaagct gcggtaagtt ttccaggctc    1800
aaaaactatg cctggctgtt tttttttta gaagggatat ggacatcgca cattaaggaa    1860
tattaaagat aacaggatgg acattcggat gtaaaaggaa taagcgaaac ctttagcaga    1920
tgtgagttaa tgcagtctcg tataattcgg tggtgctgat taggttatcg taaggaacaa    1980
cacgattgat ctctcatccg cgtcccagca atcaggccta tgtccctctc ctgtggccag    2040
ctcactggct gtgcactgtg cgattctaag tgctacagtc gtgagcagat caatggatcg    2100
gggctcgcgc aacactactg taattaaata ttcgtttatg aattatgcaa atatgcacag    2160
ataatatata cagggatgca cagacatact cctatgcacc gatacacagg cacataggca    2220
gatgtcgaca ttaacgaata tacaggcacg gacctccagg aacatatgga aaatacctca    2280
tcgcagagac gcttatgcag gagtaatctg cgttaagtcg ttactggatt gtaacggcta    2340
```

```
-continued tccggagact ctcttcccct tttgcttgtt cactgtgcgg cattattaca tttacaccgg    2400
taatgctgcg catgaaagag cgaacggaac gaggctcgta cgacattaca agaatagttt    2460
gaattc                                                              2466
```

ASSAY METHODS FOR DETECTION OF A VIRUS IN AN AVIAN TISSUE SAMPLE

The present invention relates to assay methods and, in particular, to methods for detecting the presence of a virus, especially Marek's disease virus (MDV), in an avian tissue sample.

BACKGROUND

Marek's disease virus (MDV) is a herpesvirus, which causes lymphoproliferative disease in chickens. Even after the introduction of vaccines against MDV, the infection still causes considerable losses in the poultry industry. MDV is divided into three serotypes, all of which establish latent infections. Serotype 1 includes oncogenic viruses, serotype 2 non-oncogenic viruses and serotype 3 includes the turkey herpesviruses (HVT) (Bülow et al (1976) Zentralblatt für Veterinarmedizin, 23B, 391-402).

The traditional diagnosis of Marek's disease is based on the clinical signs and pathological alterations. However, more specific methods for surveillance of the prevalence of MDV would be desirable. The detection of viral antigen in the feather follicle epithelium by the agar gel precipitation test has been described by Haider et al (1970) Poultry Science, 49, 1654-1657. The different serotypes can be differentiated by the agar gel precipitation test (Lee et al (1983) Journal of Immunology, 130, 1003-1006), but the sensitivity of that test is inferior to that of enzyme-linked immunosorbent assay (ELISA) and DNA hybridization (Davidson et al (1986) In: Current research on Marek's disease. Proceedings of the 5th International Symposium on Marek's Disease (pp. 311-316). Tallahassee: Rose Printing Company, Inc.).

The preferred samples for virus isolation are buffy-coat cells, which can be co-cultivated with susceptible primary cell cultures. Immunofluorescent assay (Kitamoto et al (1979). Biken Journal, 4, 137-142) or ELISA (Cheng et al (1984) Avian Diseases, 4, 900-911), can be used for subsequent identification of the MDV serotype. Alternatively, the serotype can be identified by restriction endonuclease analysis (Ross et al (1983). Journal of General Virology, 64, 2785-2790) or polymerase chain reaction (PCR) (Wang et al (1993) Molecular and Cellular Probes, 7, 127-131. In situ hybridization has been used for detection of MDV genome in infected tissue (Endoh et al (1996) Journal of Veterinary Medical Science, 58, 969-976; Ross et al (1997) Journal of General Virology, 78, 2191-2198), but this technique is probably too laborious for routine diagnoses. (Davidson et al (1995) Avian Pathology, 24, 69-94; and Davidson et al (1996) In: Current research on Marek's disease. Proceedings of the 5th International Symposium on Marek's Disease (pp. 311-316). Tallahassee: Rose Printing Company, Inc.), applied MDV serotype 1-specific PCR techniques to full blood and tumour tissue samples from commercial chicken and turkey flocks, the majority of which had neoplastic disease. Wang et al (1993) Molecular and Cellular Probes, 7, 127-131; Young, P. & Gravel, J. (1996) In Current research on Marek's disease. Proceedings of the 5th International Symposium on Marek's Disease (pp. 308-310). Tallahassee: Rose Printing Company, Inc.; and Silva, R. F. & Witter R. L. (1996) In Current research on Marek's disease. Proceedings of the 5th International Symposium on Marek's Disease (pp. 302-307). Tallahassee: Rose Printing Company, Inc., applied a MDV serotype 1-specific PCR protocol to various tissues of chickens experimentally inoculated with the JM/102 strain.

Handberg et al (2001) Avian Pathology 30: 243-249 describe the use of serotype 1- and serotype 3-specific PCR for the detection of MDV in chickens. Tissue samples were taken from blood (buffy-coat cells), spleen, liver, skin, feather tips and ovaries.

DESCRIPTION OF THE INVENTION

The present invention provides further methods for detecting a virus, especially MDV, in avian tissue samples.

In a first aspect the invention provides a method of detecting a virus in an avian tissue sample comprising: extracting genetic material from an avian tissue sample; and testing the extracted genetic material to detect any genetic material from the virus; characterised in that the avian tissue sample is derived from one or more feathers of the axillary tract.

By using feather samples the test can be carried out on live animals. Sampling of feathers is simple, quick and practical under field conditions. Feather samples can be placed in a suitable container and tested immediately or stored for future testing, as desired. By contrast, sampling blood requires great care to prevent blood clots forming, including transport of blood under cool, controlled conditions. Blood clotting leads to negative test results. Internal organ samples, such as spleen and tumour samples, must be transported on wet ice, which is impractical under field conditions.

By selecting axillary tract feathers from which to derive a tissue sample, the invention provides significant advantages over known methods which take tissue samples from different parts of the bird.

Surprisingly, we have found that virus can be detected in axillary tract feathers at higher levels than in other feathers and therefore virus can be detected in axillary tract feathers according to the invention when it cannot be detected in other tissue samples, including other feathers. Accordingly, the methods of the invention are particularly suitable for monitoring the extent to which a flock of birds has been immunised effectively with MDV vaccine, by detecting the presence of the vaccine strain in axillary tract feather tissue samples.

By "avian" we include any bird, but preferably birds which are produced commercially, especially poultry such as chickens, turkeys, ducks, etc.

By "axillary tract feathers", we include the meaning of the feathers located in the region of a bird marked "axillary" in the accompanying feathering diagram (FIG. 1). Preferably, the axillary tract feather selected is a "pin feather", that is, an immature growing feather. The term "pin feather" will be familiar to skilled persons. For example, van Tyne J & Berger A J (1959) Fundamentals of Ornithology, John Wiley, New York refer to a pin feather as "a new, growing feather, still not completely unsheathed". Lucas A M & Stettenheim P R (1972) Avian Anatomy, Integument Part 1, US Government Printing Office, Washington, pp 199-200 remark "The new feather is tightly furled inside a sheath while it forms. As it appears above the skin, it has a long conical shape with a blunt tip and a slightly moist surface. A feather at this stage in any generation is often called a pin feather". (See also FIG. 1(a), which is taken from Lucas & Stettenheim (1972)).

Preferably, the axillary tract feathers are taken from chicks which are advantageously less than a month old.

In a preferred embodiment, the method is performed on samples taken from chicks on or prior to 13 days post-immunisation, preferably at between 8 days to 12 days post-immunisation, more preferably at between 9 to 11 days post-immunisation, i.e. on days 9, 10 or 11 post-immunisation.

Preferably, the method provides quantitative information on the amount of virus, especially MDV, in the sample.

Preferably, the method is specific for MDV serotype 1, and more preferably the method is specific for MDV-1 Rispens strain CVI 988. The latter strain is a commercial vaccine strain produced by Fort Dodge, Iowa, USA which is available from the American Type Culture Collection (ATCC), Mannassas, Va., USA.

Advantageously, the method involves the use of a PCR reaction. Preferably, before said PCR reaction is carried out, the extracted genetic material to be tested is treated with an agent to overcome the inhibitory effect of any feather tissue factor which may be present. This inhibitory effect appears to be associated with melanin and can therefore be a particular problem when feathers from brown birds are sampled. Preferably, the agent is selected from one or more of bovine serum albumin; porcine (pig) albumin; and ovine (sheep) albumin.

Skilled persons will be aware of a range of detection methods for detecting viral, especially MDV, genetic material which could be used in the methods of the invention, such as the methods of Handberg et al (2001) supra. A particularly preferred method for detecting MDV-1 strain CVI 988 is as follows:

(i) providing forward and reverse primers for a nucleic acid polymerase, which primers are selected from the nucleotide sequence which flanks the 132 bp repeat nucleotide sequence of MDV;

(ii) amplifying nucleic acid sequences between the primers;

(iii) detecting the number of 132 bp repeat sequences in the amplified nucleic acid sequences; and (iv) relating the number of 132 bp repeat sequences to the identity of the viral nucleic acid and thereby identifying the type of MDV in the tissue sample, multiple copies of the 132 bp repeat sequence being indicative of MDV-1 strain CVI 988.

A preferred quantitative method for use in detecting MDV according to the present invention comprises:

(a) providing a polynucleotide sequence which is capable of binding specifically to a MDV-specific target polynucleotide;

(b) contacting the extracted genetic material with a probe whereby the probe binds specifically to its target MDV polynucleotide;

(c) determining whether the probe has bound to its target MDV polynucleotide; and (d) determining whether the sample contains MDV on the basis that the presence of the target polynucleotide indicates the presence of MDV in the sample.

Step (d) preferably provides a quantitative determination of the amount of virus in the sample.

Advantageously the step of determining whether the probe has bound to a target polynucleotide comprises amplifying a region of the target polynucleotide, which region comprises the binding site of the probe.

Preferably the probe has the sequence 5' AGA CCC TGA TGA TCC GCA TTG CGA CT 3' (SEQ ID No. 1).

Preferably, amplification is primed by the following primers:

Forward primer (GGT CTG GTG GTT TCC AGG TGA—SEQ ID No. 2) which is located at NT positions 1341-1361 in the GA strain Meq gene sequence.

The GA (Georgia) strain was a 1964 isolate from Georgia, from an ovarian tumour. Reference: C. S. Eidson & S. C. Schmittle (1968). Studies on acute Marek's disease. I. Characteristics of isolate GA in chickens. Avian Diseases 12; 467-476.

Reverse primer (GCA TAG ACG ATG TGC TGC TGA—SEQ ID No. 3) is located at NT positions 1413-1393.

Advantageously, the probe is labelled fluorescently and the step of determining whether the probe has bound to a target polynucleotide comprises determining the fluorescent emissions of the probe.

Two fluorescent dyes are brought into physical proximity by direct conjugation at opposite ends of a short oligo probe (5' reporter fluorochrome, usually 6-FAM, and 3' quencher fluorochrome, usually TAMRA). When the high-energy fluorophore (FAM) is excited at 488 nm, instead of the expected fluorescence emission at 520 nm the captured energy is transferred to the lower energy fluorophore (TAMRA) and is emitted at 580 nm (fluorescence resonance energy transfer, FRET, has occurred). Using the fluorescein/rhodamine reporter/quencher combination, FRET will effectively occur even when the groups are separated by 25-30 bases of DNA. During the course of a TaqMan™ assay the two fluorophores are physically detached from each other by the 5'-nuclease action of Taq DNA polymerase—after which 488 nm stimulation results in visible FAM emission at 520 nm.

Dual-labeled probes usually have a 5'-reporter dye, such as FAM, TET, HEX, JOE or VIC and a 3'-quencher group, such as TAMRA or Dabcyl (a universal quencher).

Suitable fluorescent labels are within the common general knowledge of skilled persons. The following reagents are available from Sigma-Aldrich, UK: HEX stands for hexachloro-fluorescein; TET stands for tetrachloro-fluorescein; Joe is 6-carboxy-4',5'-dichloro-2',7'-dimethoxyfluorescein; ROX is 5-carboxy-Rhodamine; dabcyl is 4-((4-(dimethylamino)phenyl)azo)benzoic acid.

Structures and further information on all of these are available on the molecular probe website www.probes.com. VIC dye is available from Applied Biosystems.

6-FAM=6-carboxyfluorescein; (a phosphoramidite); yellow-green dye; absorbance maximum=494 μm, emission maximum=525 nm HEX=a phosphoramidite; pink dye; absorbance maximum=535, emission maximum=556

TET=a phosphoramidite; orange dye; absorbance maximum=521, emission maximum=536

VIC=absorbance maximum 538, emission maximum=554

JOE=absorbance maximum 521, emission maximum=547

TAMRA=6-carboxy-tetramethyl-rhodamine; absorbance maximum=555, emission maximum=580

Dabcyl=absorbance maximum=453, no maximum emission (universal quencher)

From the foregoing description it will be apparent that an important aspect of the methods of the invention is the use of avian tissue samples which are more convenient and useful than avian tissue samples used previously for detecting viral, especially MDV, infection. Accordingly, further aspects of the invention relate to the provision of avian tissue samples.

In a second aspect the invention provides an isolated avian tissue sample from one or more feathers from the axillary tract.

By "isolated" we include the meaning that the tissue sample is free of a substantial amount of the material with which it is normally associated in nature. For example, the tissue sample may be stored in a container, or be derived from the original axillary tract feather by a variety of isolation; extraction and/or purification methods.

Preferably the isolated tissue sample consists of the proximal portion (the non-barbed portion which is attached to the skin and which contains the pulp—see accompanying figures). Accordingly it is preferred that the proximal portion of the axillary tract feather is isolated from the distal (barbed) portion of the feather. This is easily achieved simply by cutting off the proximal portion of the feather with a pair of scissors and discarding the distal portion.

In a third aspect the invention provides a genetic material-containing extract from an avian tissue sample wherein the extract is taken from a sample of tissue as described in relation to the second aspect of the invention.

It will be appreciated that samples according to the second and third aspects of the invention may be collected and/or prepared in the field, or transported to a separate location, such as a laboratory, for preparation and testing. Hence, further aspects of the invention relate to samples according to the second and/or third aspects of the invention stored in a form suitable for transport to a separate location.

The feathers could be stored complete (e.g. in 20 ml Sterilin universal plastic tubes), or after cutting off the proximal portion required for DNA preparation (e.g. in 1 ml Eppendorf snap-cap or screw-cap tubes). Alternatively, the feathers could be stored in heat-sealed or tied plastic bags. For short-term storage (e.g. 1 week), the feathers could be stored at 4° C., but, for longer periods of storage, they should be stored frozen at −20° C.

The DNA should be stored at −20° C. in screw-cap or snap-cap 0.5 ml or 1.5 ml Eppendorf tubes, in Tris-EDTA buffer or, if the DNA is to be used in Taqman analysis, in water since EDTA will inhibit the Taqman reaction.

Advantageously, the results of the methods are furnished in an intelligible format. Preferably, the results are recorded or stored on an information carrier. However, the step of furnishing the results could be by communicating the results orally.

By "information carrier", we include any means of storing information, such as paper, a computer disk; an internet-based information transfer system, such as an e-mail or internet page, or electronic file, etc. Of course, an "intelligible format" is also intended to embrace encrypted information which can be deciphered with an approximate key.

Examples embodying certain aspects of the invention will now be described with reference to the following figures in which:

FIG. 1(a) shows the development of feathers above the skin, during the first four generations. A circle indicates a feather that is still growing; a dot, a feather that is fully grown.

FIG. 1(b) is a diagram of the feathering pattern in chickens which shows the axillary tract.

The axillary tracts lie on the underside of the chick and extend, each side, from the lower neck to the upper abdomen, underneath the wings and alongside the breastbone. FIG. 1 is taken from the book 'Bird Structure: An approach through evolution development and function in the fowl'. D. A. Ede, Publisher: Hutchinson Educational, 1964. The feathering pattern is the same in all birds.

Figure 2A:
Figure 2B:
Figure 2C:
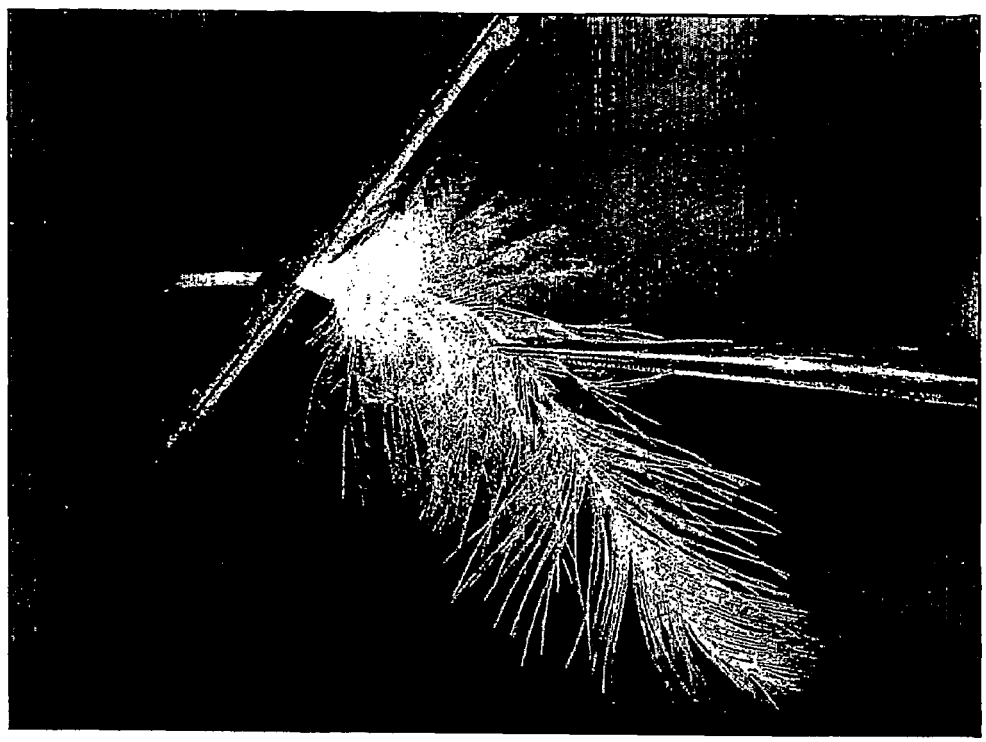
Figure 2D:
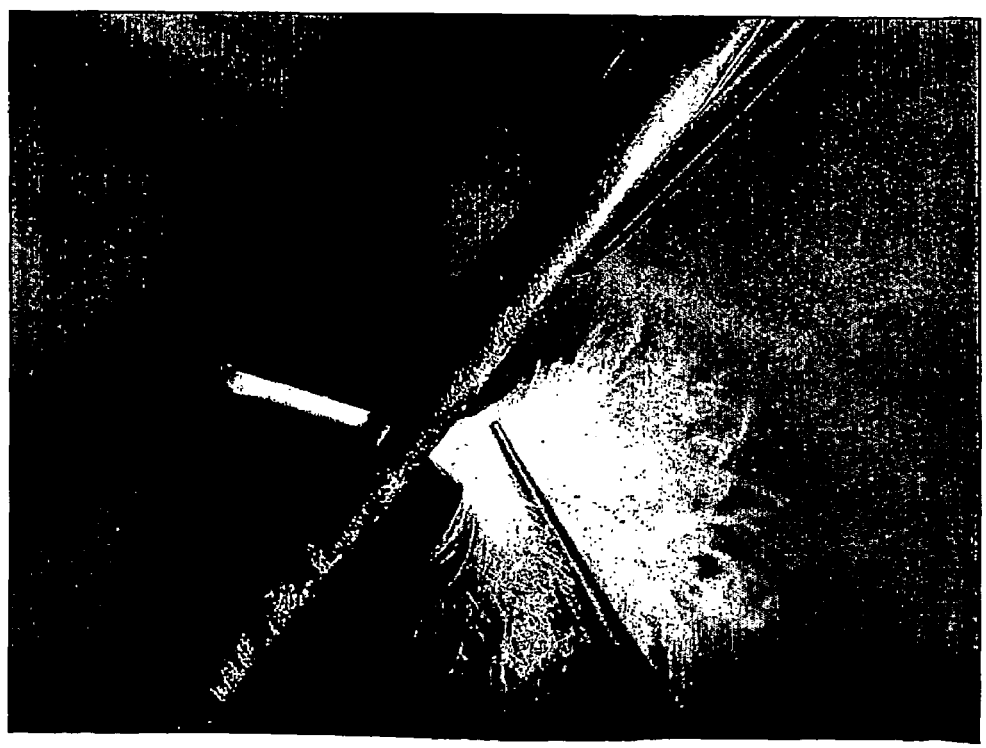
Figure 3:
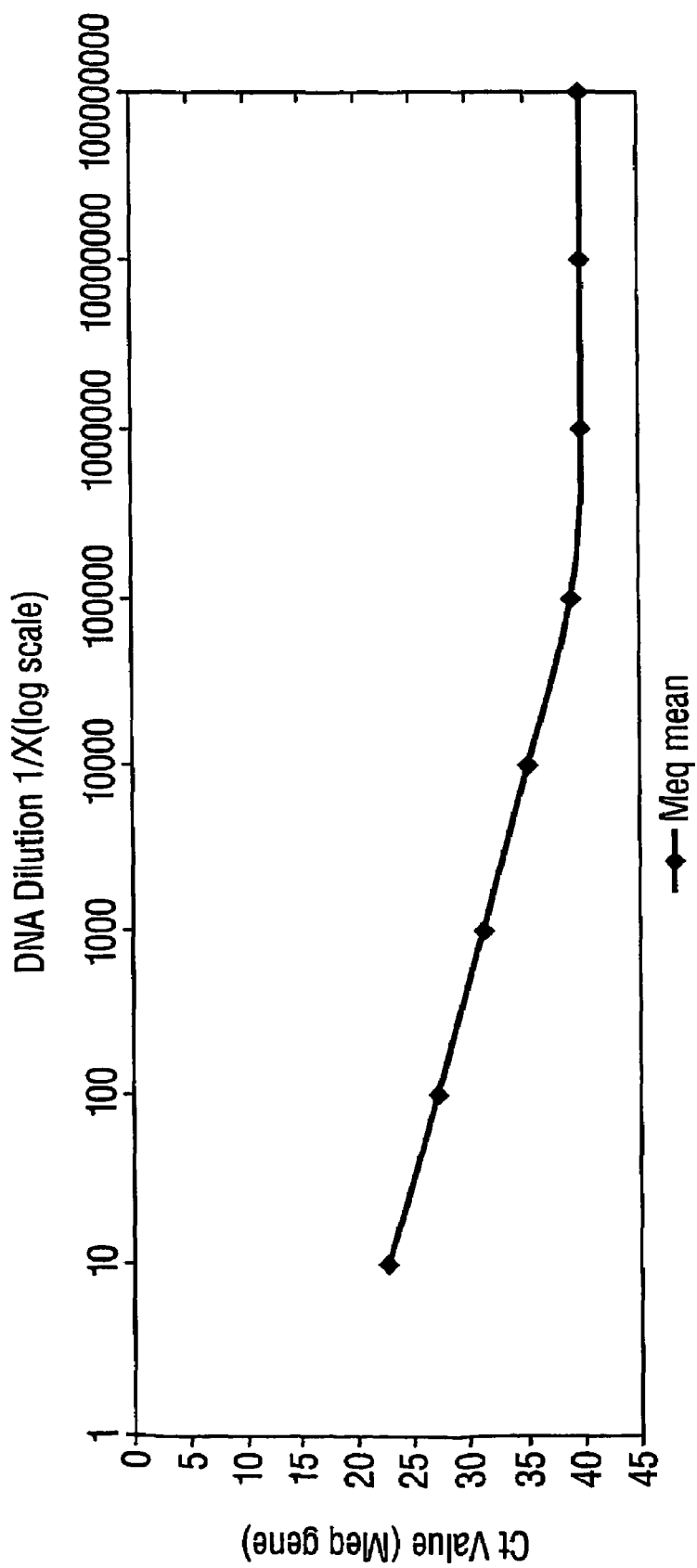
Figure 4:
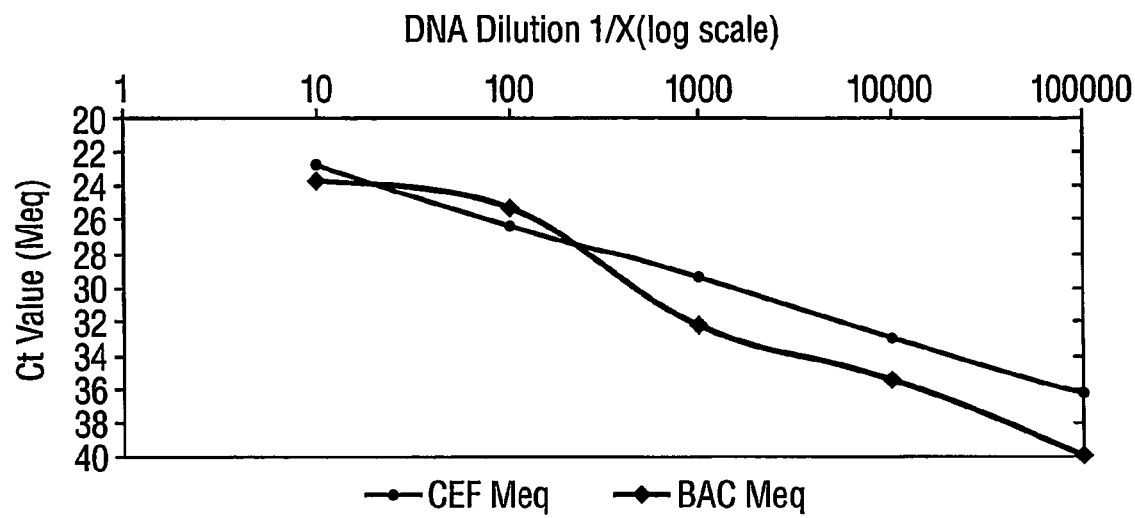

FIGS. 2(a) to 2(d) are photographs of the axillary tract feathers and close ups of individual feathers showing the portions which are retained to provide tissue samples according to the invention. FIGS. 2(a) and 2(b) demonstrate the axillary tract feathers. FIGS. 2(c) and 2(d) demonstrate the part of the feather taken for analysis.

FIG. 3:

Shows a dose response of serotype CVI988 vaccine as detected by Meq primers (78 bp product) with Taqman technique. CVI988 vaccine was harvested from a bacterial artificial chromosome (BAC) vector.

This experiment was performed to test/optimise the use of the Meq Taqman primer/probe set. BAC10 DNA was used as the target DNA since it was known to contain many copies of the viral genome.

Taqman assay was used to detect the Meq gene in DNA derived from Rispens virus genome cloned into a Bacterial Artificial Chromosome (BAC10). The DNA was used in ten-fold dilutions. During each cycle of real-time PCR, the reporter fluorochrome FAM is released and able to fluoresce. Therefore, with each cycle, fluorescence intensity increases. The Ct value (the cycle at which fluorescence passes a fixed threshold) is a measure of the starting copy number of the target sequence. The lower the Ct value, the higher the starting copy number of target sequence. A Ct value of 40 indicates that no target sequence, or an undetectable amount of target sequence, is present. This figure shows that dilutions of this DNA preparation between 1:10 and 1:10000 gave a detectable amount of Meq PCR product. The Ct value increases linearly with increasingly dilute DNA.

FIG. 4:

Dose response of CVI988 vaccine in chicken embryo fibroblasts (CEF) and bacterial artificial chromosomes (BAC). This experiment was performed to test/optimise the use of the Meq Taqman primer/probe set on DNA derived from Rispens-MDV infected cells.

Taqman assay was used to detect the Meq gene in DNA derived from BAC10, and in DNA derived from Rispens MDV-infected chick embryo fibroblast (CEF) cells. The DNA was used in ten-fold dilutions. This figure shows that for both BAC10 DNA and Rispens-infected CEF DNA, the Ct value increases linearly with increasingly dilute DNA.

FIG. 5:

Dose response of CVI988 vaccine in chicken spleen and CEF. This experiment was performed to test/optimise the use of the Meq Taqman primer/probe set on DNA derived from tissue samples from Rispens-MDV infected chickens.

Taqman assay was used to detect the Meq gene in DNA from a spleen of a Rispens-inoculated chick (11 dpi), and an age-matched uninoculated chick. DNA from Rispens-infected CEF cells was used as a positive control. The DNA was used in ten-fold dilutions of 1 mg/ml stocks and 1 μl was used per reaction. Although the Ct values for the uninoculated spleen DNA were lower than 40, they clearly did not increase with increasing concentrations of DNA. However, Meq detection in the inoculated spleen DNA rose significantly above this baseline when the DNA was used neat, or at 1:10 dilution. We thus established that, for Taqman analysis of DNA taken from tissue samples of MDV-inoculated chicks, we would use 1 μl DNA from a 1 mg/ml stock (i.e. 1 μg) DNA per reaction.

FIG. 6:

Time-course of replication of CVI988 vaccine in chicken feathers demonstrating peak replication 15-20 days post infection. This experiment was performed to follow the time-course of Rispens MDV-infection in feather axillary tracts of inoculated chicks by Taqman assay.

Taqman assay was used to detect the Meq gene in DNA prepared from feather tips of chicks at 0 (uninoculated), 10, 15, 20 and 28 dpi post inoculation with Rispens. A group of five chicks were sampled at each time-point (four chicks at 0 dpi). 1 μg DNA was used in the Taqman assay. Mean Ct values for each group are plotted. The Ct values decrease from 0-15 dpi, then increase again from 20-28 dpi, showing a peak of infection 15-20 dpi.

FIG. 7:

This experiment was performed to follow the time-course of Rispens MDV-infection in feather axillary tracts of inoculated chicks by 132 bp repeat PCR.

DNA was prepared from feather tips of Rispens-inoculated chicks at 0 (uninoculated), 10, 15, 20 and 28 dpi. A group of five chicks were sampled at each time-point (four chicks at 0 dpi). 1 μg DNA was used in PCR (including 10 μg BSA per reaction) and the samples run on a 1% agarose gel containing ethidium bromide.

(M)=Lambda molecular size markers, (−)=water (negative control), (+)=Rispens BAC10 DNA (positive control). Days post infection are indicated underneath the gels.

(a) To confirm the PCR-quality and quantity of each DNA sample, PCR was performed to detect an endogenous retrovirus sequence present in all chicken cells. The 360 bp endogenous retrovirus product was detected in all of the feather samples confirming the PCR-quality of each samples.

(b) 132 bp repeat PCR was performed. The lane marked (+) shows the 132 bp repeat ladder PCR products obtained with Rispens BAC10—six copies are clearly distinguished. The negative control shows no PCR product, as do three of the four uninoculated chicks. The fourth uninoculated chick shows a faint product band equivalent to 3 copies of the repeat, indicating that the chick was contact-infected by the inoculated chicks housed in the same room. All of the inoculated chicks were 132 bp repeat positive at 11, 15, 20 and 28 dpi. The PCR product representing a certain repeat copy number predominated in many cases and the number of copies represented by this predominant product varied between samples. This indicates that sub-clones of the inoculum virus, with a set number of repeats, come to predominate in different chicks.

FIG. 8:

Graph showing a standard curve for Meq gene reaction using Rispens BAC10 DNA

FIG. 9:

Graph showing a comparison of Rispens virus load in various feather tracts of individual chicks at (A) 8, (B) 13, (C) 19 and (D) 26 days post vaccination.

FIG. 10:

Graph showing Rispens virus load in various feather tracts determined by real time PCR for Meq gene plotted as (A) on a logarithmic scale and (B) on a linear scale. Mean values (+SEM) for four vaccinated chicks.

EXAMPLE 1

Quantitative PCR Assay for MDV-1

Taqman™ quantitative PCR is an established technique used to quantify the amount of starting PCR target by determining the number of PCR cycles required to reach a fluorescence threshold (defined mathematically by the Ct value). A higher copy number of target sequence in the sample requires fewer PCR cycles to reach the Ct threshold.

The Taqman primers and probe were designed from the Meq gene sequence of the MDV strain GA (see later). This sequence is published in: Jones D, Lee L, Liu J L, Kung H J, Tillotson J K. Marek disease virus encodes a basic-leucine zipper gene resembling the fos/jun oncogenes that is highly expressed in lymphoblastoid tumors. Proc Natl Acad Sci USA. 1992 May 1; 89(9):4042-6. The Sequence Accession No. is: M89471 (SEQ ID No. 9). The Applied Biosystems 'Primer Express' software was used to select the optimum primer/probe sequences from the Meq sequence.

The specific primers used in this analysis multiply a 73 bp sequence in the meq gene of MDV serotype 1 virus. This region is common to both vaccine strains and field isolates.

The experiments described use CVI 988 vaccine as an example of serotype 1 Marek's disease virus. The results can be applied to all serotype 1 Marek's viruses because the area of the sequence the primers are directed against is conserved in MDV serotype 1 viruses.

Protocol for Taqman™ Meq Gene PCR Analysis on Feather Tip Samples

1. Materials Required:

Reagents:
TNE buffer (store at room temperature) contains Tris (10 mM), NaCl (150 mM), EDTA (1 mM) and the pH is adjusted to pH 7.5 using HCl
Sodium Dodecyl Sulphate (SDS) 10% solution (store at room temperature)
Proteinase K (lyophilised powder from Sigma # P-6556, and make up a stock of 20 mg/ml in water, stored at −20° C.)
Phenol pH 7.9 obtained from Sigma (catalogue no. P-4557) stored at 4° C.)
Chloroform (stored at −20° C.)
3M Sodium Acetate pH5.2 (stored at room temperature)
Filtered neat ethanol (stored at room temperature)
Filtered 70% cold ethanol (stored at 4° C.)
PCR quality water
PCR quality water containing 800 μg/ml Bovine Serum Albumin (BSA), filtered
Ice
Taqman™ PCR core reagents—Taqman™ buffer, $MgCl_2$, dNTPs, Taq polymerase, Uracil N-Glycosylase (Perkin Elmer Biosystems)
Meq forward primer 5' GGT CTG GTG GTT TCC AGG TGA 3' (SEQ ID No. 2) (MWG Biotech)
Meq reverse primer 5' GCA TAG ACG ATG TGC TGC TGA 3' (SEQ ID No. 3) (MWG Biotech)
Meq probe 5' FAM AGA CCC TGA TGA TCC GCA TTG CGA CT 3' (SEQ ID No. 1) TAMRA (Sigma-Genosys Ltd)
(FAM & TAMRA are the fluorescent tags)
6-FAM=6-carboxyfluorescein; (a phosphoramidite); yellow-green dye; absorbance maximum=494 nm, emission maximum=525 nm TAMRA=6-carboxy-tetramethyl-rhodamine; absorbance maximum=555, emission maximum=580
5'FAM-3'TAMRA labelled probes are available from: Sigma-Genosys Ltd. (London Road, Pampisford, Cambridgeshire, CB2 4EF, UK. Tel. 01223 839200)
5'VIC-3'TAMRA labelled probes are available from: Applied Biosystems Ltd. (Kelvin. Close, Birchwood Science Park North, Warrington, Cheshire, Wash3 7PB)

Other Suppliers are:
Integrated DNA Technologies (IDT) 1710 Commercial Park, Coralville, Iowa, 52241, USA
Oswel Research Products Ltd.: Lab 5005, Medical and Biological Sciences Building, University of Southampton, Boldrewood, Bassett Crescent East, Southampton, SO16 7PX, Tel: 02380 592984

Equipment
Sterilin 20 ml plastic universal tubes
Clean scissors & forceps
Water bath set to 50° C.
Micro centrifuge
1.5 ml snap cap Eppendorf tubes (autoclaved)
1.5 ml screw-cap Eppendorf tubes (autoclaved) 0.5 ml snap-cap Eppendorf tubes (autoclaved)
Vacuum/freeze-drier (not essential)
Spectrophotometer
Dedicated PCR cabinet, pipettes and autoclaved tips
Thermo-fast 96-well PCR plate and caps (Perkin Elmer/Applied Biosystems)
ABI Prism 7700 Sequence Detector (Perkin Elmer/Applied Biosystems)

2. Collecting the Feathers:
Pluck 8-10 'pin' feathers (short, newly growing feathers with plenty of pulp) from the brachial feather tract of each chicken (see figures).
Place feathers in a plastic 'universal' tube for transport back to the laboratory.

3. DNA Preparation from Feather Tips:
Cut off and save the proximal 1 cm of the feather (i.e. the non-barbed part which is attached to the skin and which contains the pulp—see photographs). Discard the distal barbed part of the feather.
For each chicken, place the 8-10 saved feather ends in a 1.5 ml snap-cap Eppendorf tube.
Add 500 µl proteinase K sample buffer (TNE buffer containing 0.5% SDS) containing 100 µg proteinase K (add proteinase K just before use).
Incubate at 50° C. in a water-bath for 1.5-2 hours.
Microcentrifuge the tubes (6000 rpm, 10 min), to 'pellet' feather tips & debris.
Transfer supernatant to a new snap-cap tube (if the feathers were from brown birds, the supernatants will be brown due to the presence of melanin).
Add an equal volume (500 µl) of phenol to the supernatant again.
Vortex
Centrifuge at 13000 rpm, 2 min.
Transfer the upper (aqueous) phase to a new snap-cap tube.
Add an equal volume (500 µl) of phenol to the supernatant again.
Vortex
Centrifuge at 13000 rpm, 2 min.
Transfer the upper (aqueous) phase to a new snap-cap tube.
Add an equal volume (500 µl) of cold chloroform.
Vortex.
Centrifuge at 13000 rpm, 2 min.
Transfer the upper phase to a 1.5 ml screw-cap tube.
Add 1 ml filtered 100% ethanol.
Add 50 µl of 3M Sodium Acetate.
Gently mix by inverting the tube, and leave at room temperature for 20 minutes (the DNA will become visible as it precipitates).
Centrifuge 13000 rpm, 2 minutes, to pellet the DNA (if white chickens were used, pellet will be white; if brown chickens used, pellet brown).
Discard the supernatant.
Rinse the pellet twice with 500 µl of 70% cold ethanol, by gently running the ethanol down the side of the tube, then pouring off (take care not to dislodge the DNA pellet).
Cover the open top of the tube with Parafilm, and make several puncture holes in the Parafilm using a needle.
Place tubes in a vacuum drier for about 5 minutes to dry the pellet (alternatively air-dry).
Re-suspend the pellet in 50 µl PCR quality water by gently vortexing.
Determine the concentration of the DNA preparation using a spectrophotometer.
Adjust the concentration to 1 mg/ml in water.
Store at −20° C.

4. TaqMan™ Quantitative PCR Assay (Perkin Elmer Biosystems)
Set up reactions in a PCR-dedicated cabinet, using PCR-dedicated pipettes and autoclaved tips
Work on ice Prepare master mix containing the following reagents for the appropriate number of samples—set up duplicate reactions for each sample (volumes given per reaction):

| Component | Volume per 25 µl reaction | Final Concentration |
|---|---|---|
| Taqman buffer | 2.5 µl | |
| MgCl$_2$ (5 mM) | 5.0 µl | 1.0 mM |
| dATP (10 mM) | 0.5 µl | 0.2 mM |
| dCTP (10 mM) | 0.5 µl | 0.2 mM |
| dGTP (10 mM) | 0.5 µl | 0.2 mM |
| dUTP (10 mM) | 0.5 µl | 0.2 mM |
| Water containing 800 µg/ml BSA | 11.6 µl | ~10 µg BSA/reaction |
| Meq probe (10 µM) | 0.5 µl | 0.2 µM |
| Meq forward primer (10 µM) | 1.0 µl | 0.4 µM |
| Meq reverse primer ((10 µM) | 1.0 µl | 0.4 µM |
| Taq Gold DNA pol (5 U/µl) | 0.13 µl | 26 U/ml |
| Uracil N-glycosylase (1 U/µl) | 0.25 | 10 U/ml |

Vortex to ensure complete mixing
Place a thermo-fast PCR plate into a plate holder on ice and add 24 µl master mix to each well to be used
Add 1 µl autoclaved water to no-template-control (NTC) wells and cap these wells prior to opening any DNA samples
Add 1 µl positive control DNA (=1 µl of 1 mg/ml preparation), e.g. DNA from Rispens-infected CEF to appropriate wells and cap these wells
Add 1 µg sample DNA (=1 µl of 1 mg/ml preparation), to appropriate wells and cap
Briefly pulse plate in centrifuge
Place plate in ABI Prism 7700 Sequence Detector (Applied Biosystems) and set up computer to read FAM fluorescence (Meq probe), run samples
Thermocycling parameters

| | | |
|---|---|---|
| 50° C. | 2 min | |
| 95° C. | 10 min | |
| 94° C. | 15 sec | } × 40 |
| 60° C. | 1 min | |

Analyse data using Microsoft excel—for each sample there will be a Ct value (the PCR cycle at which the amount of fluorescent product is first detected above baseline level); calculate mean Ct value for duplicates for each DNA sample.

Figure 6:
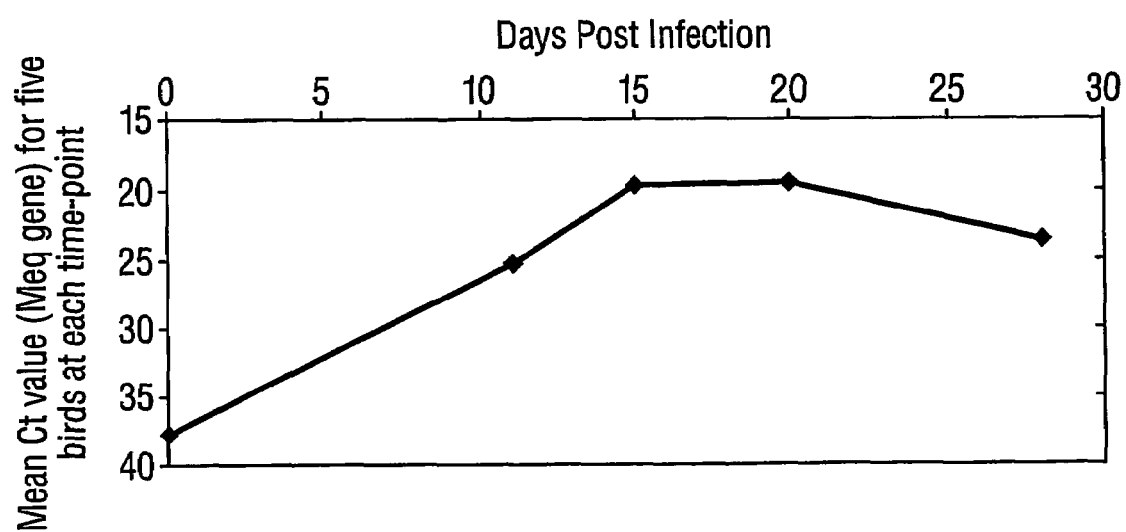

Results of the Above Experiment are Shown in FIG. 6.

Notes
The Forward primer (GGT CTG GTG GTT TCC AGG TGA—SEQ ID No. 2) is located at NT positions 1341-1361 in the GA strain Meq gene sequence. The reverse primer (GCA TAG ACG ATG TGC TGC TGA—SEQ ID No. 3) is located at NT positions 1413-1393. The probe was designed to specifically anneal between the two primers on the Meq target sequence (see FIG. 8).

During PCR, the fluorogenic probe binds between the two primers and, during each extension cycle, the 5' nuclease activity of the Taq polymerase cleaves the probe, releasing the reporter fluorochrome FAM that is then able to fluoresce.

Therefore, with each cycle, fluorescence intensity increases. The Ct value (the cycle at which fluorescence passes a fixed threshold) is a measure of the starting copy number of the target sequence: the higher the starting copy number, the lower the Ct value.

Use of Bovine Serum Albumin during PCR: feather tissues (especially those from brown chickens) contain melanin, which has been shown to be inhibitory to PCR. Use of BSA in the reaction overcomes this melanin-induced inhibition. Experiments were carried out in brown chickens. The addition of BSA followed the method of Giambernardi et al (1998). *Biotechniques* 25: 564-6.

EXAMPLE 2

Method for Detecting Specific MDV-1 (CV1 988 Vaccine) Strain

This example of the invention relates to the use of a specially modified version of the 132 base pair (bp) repeat polymerase chain reaction (PCR) test to detect the presence of CVI 988 Marek's vaccine in chicken feathers.

The 132 base pair repeat genetic sequence is located in the internal repeat long ($IR_L$) segment of the Marek's disease virus (serotype 1) genome. The complete genomic sequence of MDV 1 is described in Tulman et al. (September 2000) *J Virol*. Vol. 74 No. 17, p 7980-7988 and has been deposited in GenBank under accession no. AF 243438. CV1 988 isolates (vaccine strains) of serotype 1 Marek's disease have multiple copies of this repeat segment, whilst field strains have single copies (Silva et al (1992) *Avian Dis* 36: 521-528; and Becker et al (1993) *Virus Genes* 7: 277-287). Measuring the number of copies affords the possibility of differentiating vaccine strains from field strains. (Becker et al (1992) *J Virol Methods* 40: 307-322 and Kopacek et al (1993) *Acta Virol* 37: 191-195).

Feathers are sampled according to the enclosed figures, the proximal tips of the axillary tract feathers being used. PCR analysis (see below) demonstrated multiple copies of the 132 bp segment in animals between 11 and 28 days post vaccination. Vaccination was carried out on birds at one day of age.

An acceptable variation of the test is to use feathers in birds of any age either taken as fresh samples, or stored for testing at a later date to determine the presence of the CV1988 vaccine.

Protocol for 132 bp Repeat PCR on Feather Tip Samples

1. Materials Required:

Reagents:
TNE buffer (store at room temperature) contains Tris (10 mM), NaCl (150 mM), EDTA (1 mM) and the pH is adjusted to pH 7.5 using HCl
Sodium Dodecyl Sulphate (SDS) 10% solution (store at room temperature)
Proteinase K (lyophilised powder from Sigma # P-6556, and make up a stock of 20 mg/ml in water, stored at $-20°$ C.)
Phenol pH 7.9 obtained from Sigma (catalogue no. P-4557) (stored at 4° C.)
Chloroform (stored at $-20°$ C.)
3M Sodium Acetate pH5.2 (stored at room temperature)
Filtered neat ethanol (stored at room temperature)
Filtered 70% cold ethanol (stored at 4° C.)
PCR quality water
PCR quality water containing 800 µg/ml Bovine Serum Albumin (BSA), filtered
Taq gold DNA polymerase (5 U/µl), Taq buffer, $MgCl_2$ (25 mM) from Bio/Gene Ltd, Kimbolton, Cambridgeshire, England
dATP, dTTP, dCTP, dGTP (100 mM stocks) obtained from Promega (USA); we prepare a mix containing all four of these at 10 mM each, stored at $-20°$ C.
DNA molecular size markers
Agarose and TBE buffer
Primer sequences:

MD-132 FOR;
5' TACTTCCTATATAGATTGAGACGT-3'   (SEQ ID No. 4)

MD-132 REV:
5' GAGATCCTCGTAAGGTGTAATATA-3'   (SEQ ID No. 5)

Equipment:
Sterilin 20 ml plastic universal tubes
Clean scissors & forceps.
Water bath set to 50° C.
Micro centrifuge
1.5 ml snap cap Eppendorf tubes (autoclaved)
1.5 ml screw-cap Eppendorf tubes (autoclaved)
0.5 ml snap-cap Eppendorf tubes (autoclaved)
Vacuum/freeze-drier (not essential)
Spectrophotometer
Dedicated PCR cabinet, pipettes & autoclaved tips
Thermal cycler
Agarose gel apparatus 2. Collecting the Feathers:
Pluck 8-10 'pin' feathers (short, newly growing feathers with plenty of pulp) from the axillary feather tract of each chicken (see figures).
Place feathers in a plastic 'universal' tube for transport back to the laboratory.

3. DNA Preparation from Feather Tips:
Cut off and save the proximal 1 cm of the feather (i.e. the non-barbed part which is attached to the skin and which contains the pulp—see photographs). Discard the distal barbed part of the feather.
For each chicken, place the 8-10 saved feather ends in a 1.5 ml snap-cap Eppendorf tube.
Add 500 µl proteinase K sample buffer (TNE buffer containing 0.5% SDS) containing 100 µg proteinase K (add proteinase K just before use).
Incubate at 50° C. in a water-bath for 1.5-2 hours.
Microcentrifuge the tubes (6000 rpm, 10 min), to 'pellet' feather tips and debris.
Transfer supernatant to a new snap-cap tube (if the feathers were from brown birds, the supernatants will be brown due to the presence of melanin).
Add an equal volume (500 µl) of phenol to the supernatant
Vortex
Centrifuge at 13000 rpm, 2 min
Transfer the upper (aqueous) phase to a new snap-cap tube
Add an equal volume (500 µl) of phenol to the supernatant again.
Vortex
Centrifuge at 13000 rpm, 2 min.
Transfer the upper phase to a new snap-cap tube.
Add an equal volume (500 µl) of cold chloroform.
Vortex.
Centrifuge at 13000 rpm, 2 min.
Transfer the upper phase to a 1.5 ml screw-cap tube.
Add 1 ml filtered 100% ethanol.

Add 50 µl of 3M Sodium Acetate.

Gently mix by inverting the tube, and leave at room temperature for 20 minutes (the DNA will become visible as it precipitates).

Centrifuge at 13000 rpm, 2 minutes, to pellet the DNA (if white chickens were used, pellet will be white; if brown chickens used, pellet brown).

Discard the supernatant.

Rinse the pellet twice with 500 µl of 70% cold ethanol, by gently running the ethanol down the side of the tube, then pouring off (take care not to dislodge the DNA pellet).

Cover the open top of the tube with Parafilm, and make several puncture holes in the Parafilm using a needle.

Place tubes in a vacuum drier for about 5 minutes to dry the pellet (alternatively air-dry).

Re-suspend the pellet in 50 µl PCR quality water by gentle vortexing.

Determine the concentration of the DNA preparation using a spectrophotometer.

Adjust the concentration to 1 mg/ml in water.

Store at −20° C.

4. 132 bp Repeat PCR:

Set up reactions on ice, in 0.5 ml Eppendorf tubes, in a PCR-dedicated cabinet, using PCR-dedicated pipettes and autoclaved tips.

Prepare a 'master mix' containing the following reagents for the appropriate number of samples (volumes given per reaction):

| Component | Volume per 20 µl reaction | Final Concentration |
| --- | --- | --- |
| Forward primer (10 µM) | 1.0 µl | 0.5 µM |
| Reverse primer (10 µM) | 1.0 µl | 0.5 µM |
| 10 × Taq buffer | 2.0 µl | |
| MgCl$_2$ (25 mM) | 1.6 µl | 2 mM |
| DNTP mix (10 mM) | 0.5 µl | 0.25 mM |
| Taq gold DNA polymerase | 0.1 µl | 25 units/ml |
| Water containing 800 µg/ml BSA* | 12.8 µl | 10 µg BSA/reaction |

Vortex to ensure complete mixing.

Aliquot 19 µl 'master mix' into autoclaved 0.5 ml snap-cap Eppendorf tubes.

Add 1 µg DNA (=1 µl of 1 mg/ml preparation, or larger volume if DNA preparation less concentrated).

Vortex to ensure complete mixing.

(Our thermal cycler has a heated lid, so we do not need to overlay the reactions with mineral oil).

Run on a thermal cycler using the following cycling parameters:

| | | |
| --- | --- | --- |
| 95°C. | 2 min | 1 cycle |
| 95°C. | 1 min | |
| 50°C. | 30 sec | × 40 cycles |
| 72°C. | 1 min | |
| 72°C. | 10 min | 1 cycle |

Analyse reaction products on an agarose gel.

The results of the above experiment are shown in FIG. 7.

Notes

The sense primer is located 65 bp upstream of the repeat and the antisense primer is located 105 bp downstream of the repeat. The expected band size is therefore 302 bp for a single repeat (i.e. 65+132+105), 434 bp for a double repeat (302+132) and 566 bp for a triple repeat (434+132) etc. Rispens vaccine strain produces many tandem repeats.

EXAMPLE 3

Detection of Rispens Virus Genome in Feather Tip DNA using PCR: Comparison of Samples from Different Feather Tracts Methods Feather Sampling from Rispens-vaccinated Chicks Two-week-old Rhode Island Red chicks were inoculated with 1000 pfu Fort Dodge Rispens vaccine virus via the intra-peritoneal route. Age-matched, non-vaccinated chicks were housed in a separate room. All chicks were wing-banded in both wings, to permit identification of individual chicks throughout the experiment. At 8, 13, 19 and 26 days post vaccination, five vaccinated chicks (#921, #923, #924, #925) and one non-vaccinated chick (#946) were sampled. Approximately six pinfeathers were plucked from each of the Cervical, Humeral, Spinal, Axillary and Femoral tracts. The remaining five feather tracts were not used either because the number of feathers was too few to allow sampling on four occasions, or because it was considered unethical to pluck from delicate regions of the skin of living chicks.

DNA was prepared from the feather tips and subjected to real-time PCR to detect the virus Meq gene, as summarised below.

DNA Preparation from Feather Tip Samples

DNA was prepared from feather tips as described above. Briefly, feather tips were incubated at 50° C. for 2 hours in 500 µl TNE-SDS buffer containing 100 µg proteinase K. The supernatant was extracted with phenol, then with ice-cold chloroform. DNA was precipitated, using ethanol/sodium acetate, pelletted, vacuum dried, then resuspended to a concentration of 200 µg/ml in water.

Real-time (TaqMan) PCR Assay to Detect Meq Gene

25 µl duplex reactions were set up as described above, using Taq gold DNA polymerase and primers to amplify the viral Meq gene and the host Ovotransferrin (Ovo) gene (table 1) from 200 ng feather tip DNA. BSA was present at a concentration of 10 µg per reaction. The reaction kinetics were followed by inclusion of a FAM-fluorescent-tagged Meq probe and a VIC-fluorescent-tagged Ovo probe (table 1). There were duplicate reactions for each sample. The thermocycling parameters were: 1 cycle of 50° C. (2 min), 1 cycle of 95° C. (10 min), followed by 40 cycles of 94° C. (15 sec) and 60° C. (1 min). In addition to the feather samples under test, the reaction plate also included ten-fold dilutions of Rispens BAC10 DNA (Rispens virus genome cloned into a Bacterial Artificial Chromosome), containing a calculated number of copies of the Rispens genome.

The data were analysed using Microsoft Excel. For each reaction, the Ct value (the PCR cycle at which the amount of fluorescent product is first detected above baseline level), and thence the 40-Ct value, was obtained. A Ct value of 40 indicates that no target sequence was present. Values are presented as '40-Ct' so that a higher value equates to more copies of the viral genome.

For the Rispens BAC10 samples, 40-Ct value was plotted against number of copies of virus genome (log scale), to produce a standard curve. The equation for the linear portion of the plot was determined. For the feather samples under test, the 40-Ct values were 'normalised' according to the 40-Ct value for Ovo (a 'house-keeping gene' present in all chicken cells), to correct for slight differences in the amount of DNA used for each sample. The mean, normalised 40-Ct value for duplicate reactions was then determined and was converted to Rispens genome copy number using the standard curve.

TABLE 1

Primers and probes used in conventional and real-time PCR

| Target Sequence | Primer Name | Primer Sequence (5'-3') | Primer Location | Amplicon Size |
|---|---|---|---|---|
| MDV-1 Meq gene (based on GA sequence) | Meq forward | GGTCTGGTGGTTTCCA GGTGA (SEQ ID No. 2) | 1341-1361 | 73 bp |
| | Meq reverse | GCATAGACGATGTGCT GCTGA (SEQ ID No. 3) | 1413-1393 | |
| | Meq probe | AGACCCTGATGATCCG CATTGCGACT (5' FAM label, 3' TAMRA label) (SEQ ID No. 1) | 1366-1391 | |
| Ovotransferrin gene (Ovo) | Ovo forward | CACTGCCACTGGGCTC TGT (SEQ ID No. 6) | 4517-4535 | 62 bp |
| | Ovo reverse | GCAATGGCAATAAAC CTCCAA (SEQ ID No. 7) | 4567-4587 | |
| | Ovo probe | AGTCTGGAGAAGTCT GTGCAGCCTCCA (5' VIC label, 3' TAMRA label) (SEQ ID No. 8) | 4537-44564 | |

Results

Feather Sampling and DNA Preparation

Although it was initially planned to sample each of the ten feather tracts, it was only practicable to use the Cervical, Humeral, Spinal, Axillary and Femoral tracts. The remaining five feather tracts could not be used either because the number of feathers was too few to allow sampling on four occasions, or because it was considered unethical to pluck from delicate regions of the skin of living chicks. Sufficient pinfeathers were obtained from each tract at 8, 13 and 19 days post vaccination. By 26 days (when the chicks were almost 6 weeks old) the pinfeathers were beginning to be replaced by harder, mature feathers. Sufficient DNA was obtained from all samples, with no marked differences between amount of DNA obtained from the same number of feathers from different tracts. In order that the Meq and Ovo Ct values fell into the linear range of detection for real-time PCR, it was found necessary to dilute the DNAs to a concentration of 200 ng/μl and to use 1 μg of this stock:per for real-time PCR reactions.

To enable accurate comparison of virus load at different time-points, in different feather tracts, and in different chicks, real-time quantitative PCR was performed.

Figure 8:
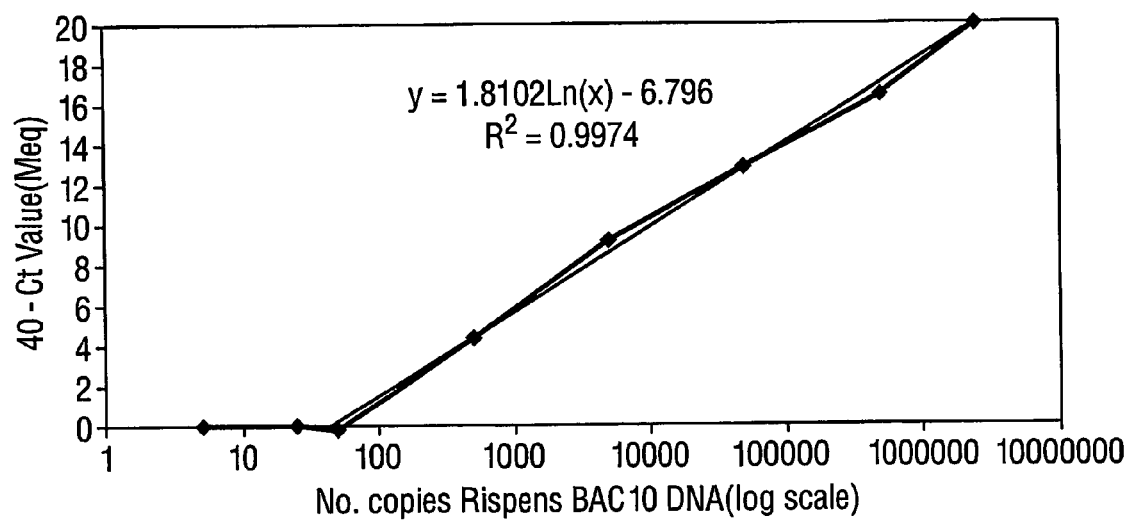
Figure 9B:
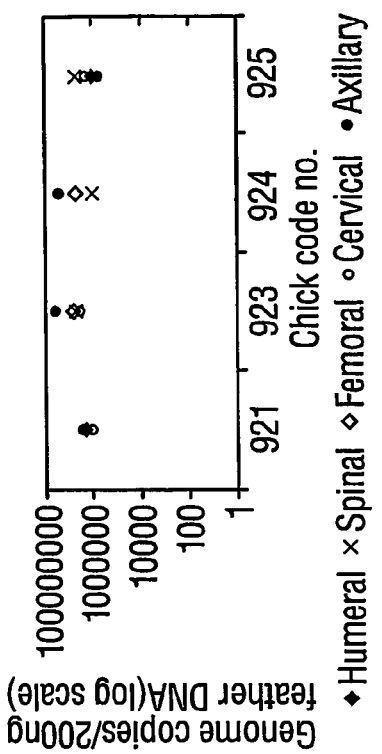
Figure 9D:
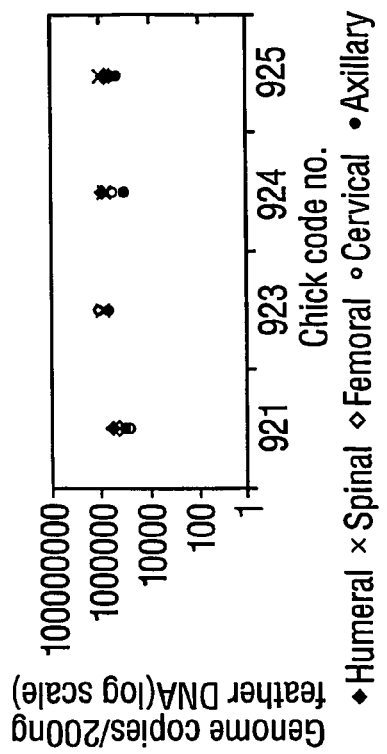
Figure 9A:
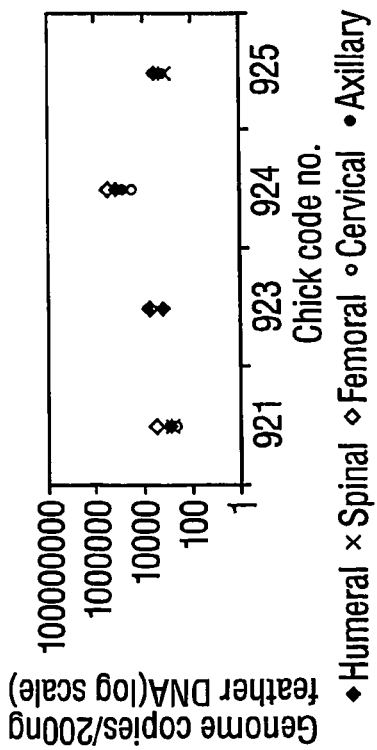
Figure 9C:
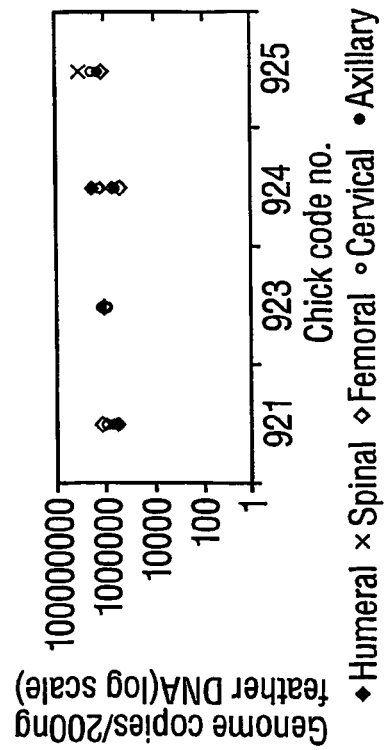

For each reaction, the 40-Ct value was calculated. For the Rispens BAC10 samples, 40-Ct value was plotted against number of copies of virus genome (log scale), to produce a standard curve (FIG. 8). The lower limit of accurate detection was 50 copies thus, any samples with a 40-Ct value of 0 contain fewer than 50 copies of the Rispens genome per 200 ng feather tip DNA.

The equation for the linear portion of the plot was: $y = 1.8102 \, \text{Ln}(X) - 6.796$. For each of the feather samples under test, the mean, normalised 40-Ct values were converted to Rispens genome copy number using this equation (see Tables 2A, B, C and D; FIGS. 9 A, B, C and D). As expected, there was considerable variation between individual chicks at any given time-point. However, the levels of virus detected in the five different feather tracts of a given individual were similar. In each chick, of the four timepoints tested, virus load was greatest at 13 days, decreasing at 19 and 26 days.

TABLE 2A

Rispens MDV copy number (8 days)
8 days post vaccination

| Chick # & feather tract | Copies of Rispens MDV genome/200 ng feather DNA | | | | |
|---|---|---|---|---|---|
| | Humeral | Spinal | Femoral | Cervical | Axillary |
| #921 | 673 | 537 | 2630 | 442 | 778 |
| #923 | 1504 | 4890 | 5127 | 5921 | 6101 |
| #924 | 112910 | 61242 | 258345 | 31425 | 62444 |
| #925 | 2603 | 1265 | 2010 | 1883 | 1583 |
| Mean | 29422 | 16983 | 67028 | 9918 | 17726 |
| SDev | 55664 | 29567 | 127552 | 14524 | 29904 |
| SE mean | 27832 | 14784 | 63776 | 7262 | 14952 |

TABLE 2B

Rispens MDV copy number (13 days)
13 days post vaccination

| Chick # & feather tract | Copies of Rispens MDV genome/200 ng feather DNA | | | | |
|---|---|---|---|---|---|
| | Humeral | Spinal | Femoral | Cervical | Axillary |
| #921 | 2133045 | 2564484 | 2432204 | 1224616 | 2511886 |
| #923 | 3814060 | 4374639 | 5998652 | 3561896 | 38349161 |
| #924 | 24768376 | 876646 | 4241591 | 24073508 | 24711780 |
| #925 | 866276 | 4478465 | 1557400 | 1856729 | 485447 |
| Mean | 7895439 | 3073559 | 3557462 | 7679187 | 16514568 |
| SDev | 11313237 | 1708035 | 1974326 | 10974035 | 18229569 |
| SE mean | 5656619 | 854018 | 987163 | 5487018 | 9114785 |

TABLE 2C

Rispens MDV copy number (19 days)
19 days post vaccination

Chick # & feather tract — Copies of Rispens MDV genome/200 ng feather DNA

| tract | Humeral | Spinal | Femoral | Cervical | Axillary |
|---|---|---|---|---|---|
| #921 | 353997 | 613762 | 1158777 | 736207 | 439542 |
| #923 | 1040917 | 1427067 | 1061134 | 1029830 | 1335442 |
| #924 | 3108135 | 891103 | 256243 | 1584386 | 391420 |
| #925 | 2958332 | 9800358 | 1469708 | 3373701 | 1705109 |
| Mean | 1865345 | 3183073 | 986466 | 1681031 | 967878 |
| SDev | 1378768 | 4424421 | 517048 | 1181980 | 655758 |
| SE mean | 689384 | 2212211 | 258524 | 590990 | 327879 |

TABLE 2D

Rispens MDV copy number (26 days)
26 days post vaccination

Chick # & feather tract — Copies of Rispens MDV genome/200 ng feather DNA

| tract | Humeral | Spinal | Femoral | Cervical | Axillary |
|---|---|---|---|---|---|
| #921 | 295801 | 193642 | 167109 | 74645 | 95940 |
| #923 | 921896 | 694141 | 541176 | 976157 | 569305 |
| #924 | 771634 | 615826 | 349598 | 343195 | 104585 |
| #925 | 353768 | 926750 | 511690 | 251692 | 236766 |
| Mean | 585775 | 607590 | 392393 | 411422 | 251649 |
| SDev | 308455 | 305928 | 172194 | 392646 | 221359 |
| SE mean | 154228 | 152964 | 86097 | 196323 | 110680 |

Figure 5:
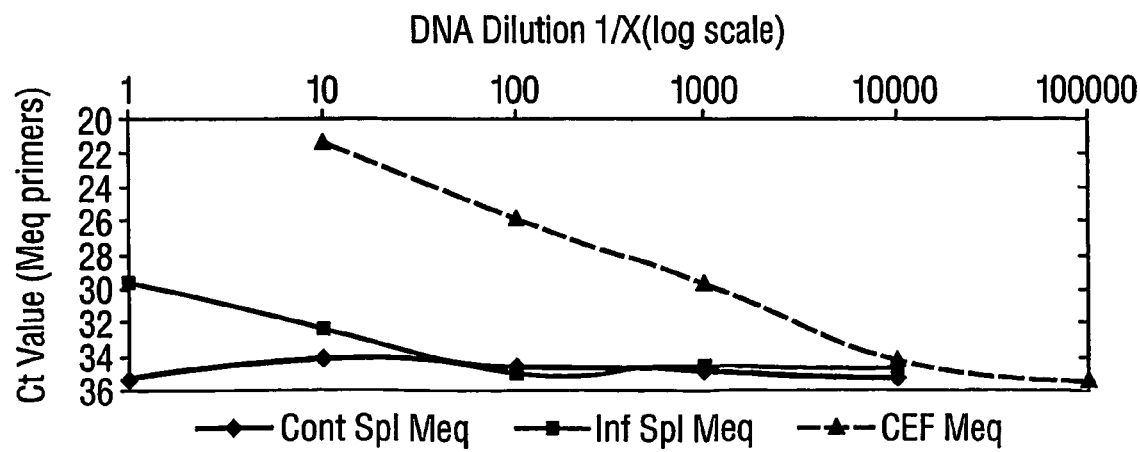
Figure 10A:
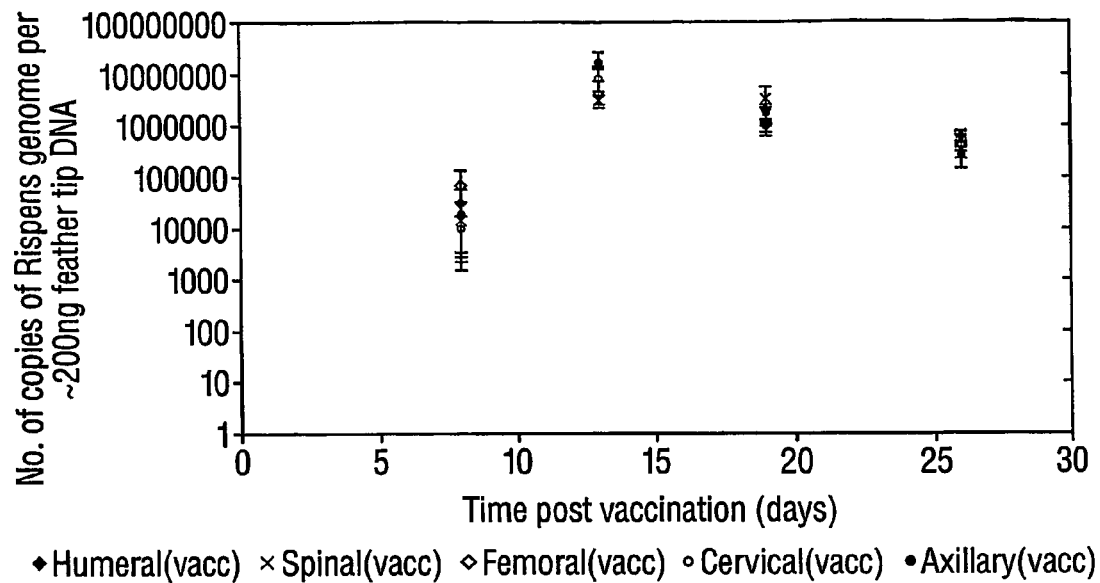
Figure 10B:
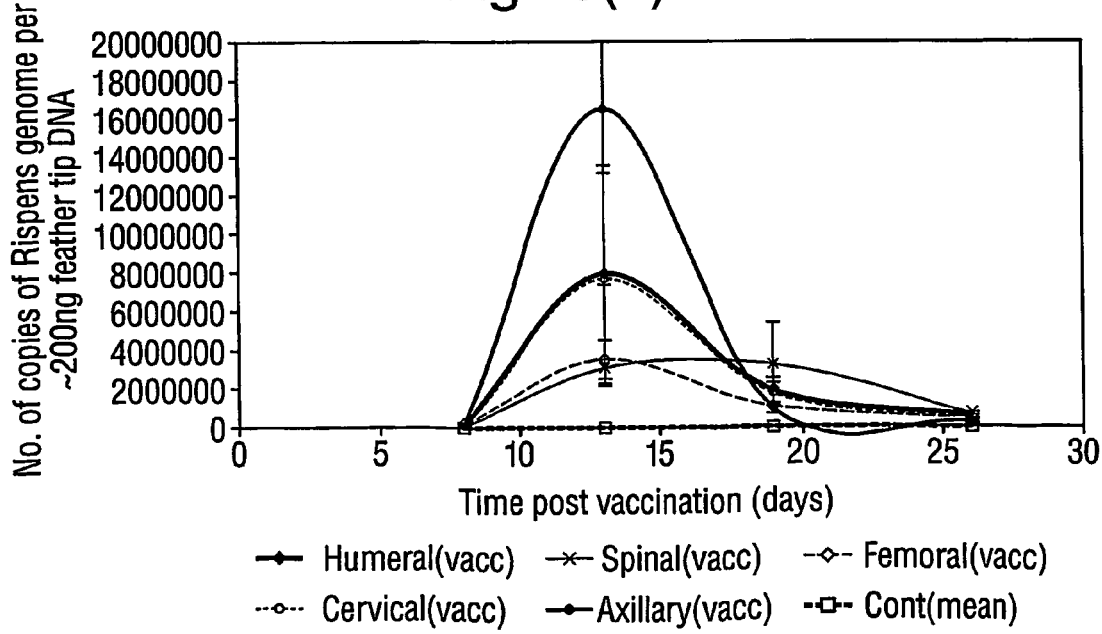

For the four vaccinated chicks, the mean genome copy number (per 200 ng feather DNA) was determined for each feather tract at each time-point, and plotted against time post vaccination using either a logarithmic scale (FIG. 5) or a linear scale (FIG. 10B). At 8 days, mean copy number was between $10^4$ and $10^5$ copies per 200 ng DNA. At 13 days, mean copy number was between $5\times10^6$ and $5\times10^7$. at 19 days, between $10^6$ and $10^7$; and at 26 days, between $10^5$ and $10^6$.

The logarithmic plot (FIG. 10A) indicated similar virus replication kinetics in each of the five feather tracts. However, differences are emphasised in linear plot (FIG. 10B). This plot shows that, at 13 days, the mean virus load for four chicks is up to four-fold greater in the axillary tracts than in the other four tracts. At this time-point, virus loads in the humeral and cervical tracts were very closely related at each time-point, and were greater than virus load in the femoral and spinal tracts. These differences between feather tracts were not apparent at 8, 19 or 26 days.

For the non-vaccinated control chick (#946) the majority of the samples gave 40-Ct values of 0, as would be expected in the absence of MDV DNA. However, for some of the samples, the 40-Ct values were up to 3 (data not shown). It is often the case in real-time PCR that 'negative' samples give a 40-Ct value above 0, and values smaller than 4 are considered 'unreliable'. Thus, although a 40-Ct value of 3 equates to ~200 copies of Rispens genome, this value is 100-fold lower than any values obtained for samples from vaccinated chicks, and can be considered negative. As seen in FIG. 5B, the mean copy number for the five feather tracts of the non-vaccinated chick does not rise above the baseline.

Summary of Real-time PCR Analysis
  Virus load in each of the feather tracts was sufficient to be detectable by real-time PCR at 8, 13, 19 and 26 days post vaccination.
  Virus load was highest in all of the tested feather tracts at. 13 days post vaccination, as compared with 8, 19 and 26 days post-vaccination.
  At 13 days post vaccination, virus load was higher in the axillary tract than in the humeral and cervical tracts (two times greater) or in the spinal and femoral tracts (four times greater).

---

The invention claimed is:

1. A method of detecting a virus in an avian tissue sample comprising: extracting genetic material from an avian tissue sample; and testing the extracted genetic material to detect any genetic material from the virus; characterised in that the avian tissue sample is derived from one or more feathers of the axillary tract.

2. A method of detecting a virus as claimed in claim 1 wherein the method provides quantitative information on the amount of the virus in the sample.

3. A method of detecting a virus as claimed in claim 1 wherein the method is specific for Marek's Disease Virus (MDV).

4. A method as claimed in claim 3 wherein the method is specific for MDV serotype 1.

5. A method of detecting MDV as claimed in claim 4 wherein the method is specific for MDV-1 Rispens strain CVI 988.

6. A method as claimed in claim 5 wherein the method comprises:
   (i) providing forward and reverse primers for a nucleic acid polymerase, which primers are selected from the nucleotide sequence which flanks the 132 bp repeat nucleotide sequence of MDV;
   (ii) amplifying nucleic acid sequences between the primers;
   (iii) detecting the number of 132 bp repeat sequences in the amplified nucleic acid sequences; and
   (iv) relating the number of 132 bp repeat sequences to the identity of the viral nucleic acid and thereby identifying the type of MDV in the tissue sample.

7. A method as claimed in claim 1 which comprises
   (a) providing a polynucleotide sequence which is capable of binding specifically to a virus-specific target polynucleotide;
   (b) contacting the extracted genetic material with a probe whereby the probe binds specifically to its target viral polynucleotide;
   (c) determining whether the probe has bound to its target viral polynucleotide; and
   (d) determining whether the sample contains the virus on the basis that the presence of the target polynucleotide indicates the presence of the virus in the sample.

8. A method as claimed in claim 7 wherein the step (c) of determining whether the probe has bound to a target polynucleotide comprises amplifying a region of the target polynucleotide, which region comprises the binding site of the probe.

9. A method as claimed in claim 8 wherein amplification is primed by the following primers:
   Forward primer (GGT CTG GTG GTT TCC AGG TGA) (SEQ ID NO:2)
   Reverse primer (GCA TAG ACG ATG TGC TGC TGA) (SEQ ID NO:3).

10. A method as claimed in claim 9 wherein the probe has the sequence
   5' AGA CCC TGA TGA TCC GCA TTG CGA CT 3' (SEQ ID NO:1).

11. A method as claimed in claim 7 wherein the probe is labelled fluorescently and wherein the step of determining whether the probe has bound to a target polynucleotide comprises determining the fluorescent emissions of the probe.

12. A method of detecting a virus as claimed in claim 1 wherein the method involves the use of a PCR reaction.

13. A method as claimed in claim 12 wherein before said PCR reaction is carried out, the extracted genetic material to be tested is treated with an agent to overcome the inhibitory effect of any feather tissue factor which may be present.

14. A method of detecting a virus as claimed in claim 13 wherein the agent is selected from one or more of bovine serum albumin; porcine (pig) albumin; and ovine (sheep) albumin.

15. The method of claim 12, wherein said PCR reaction includes bovine serum albumin (BSA).

* * * * *